United States Patent [19]

Chinai et al.

[11] 4,023,570
[45] May 17, 1977

[54] ADHESIVELY ATTACHED ABSORBENT LINERS

[75] Inventors: Kays Chinai, Burlington; James A. Ginocchio, Summit, both of N.J.

[73] Assignee: Personal Products Company, Milltown, N.J.

[22] Filed: Apr. 21, 1976

[21] Appl. No.: 678,796

[52] U.S. Cl. .................... 128/290 R; 128/290 W
[51] Int. Cl.[2] .................................. A61F 13/16
[58] Field of Search ......... 128/290 R, 290 W, 287, 128/284

[56] References Cited

UNITED STATES PATENTS

| | | | |
|---|---|---|---|
| 3,724,466 | 4/1973 | Hendricks | 128/290 R |
| 3,800,797 | 4/1974 | Tunc | 128/290 R |
| 3,805,790 | 4/1974 | Kaczmarzyk et al. | 128/290 R |
| 3,853,129 | 12/1974 | Kozak | 128/287 |
| 3,897,783 | 8/1975 | Ginocchio | 128/290 R |
| 3,967,624 | 6/1976 | Milnamow | 128/287 |

*Primary Examiner*—Aldrich F. Medbery
*Attorney, Agent, or Firm*—Jason Lipow

[57] ABSTRACT

A protective absorbent liner for nether garments is provided comprising an elongated absorbent body having the body contacting major surface and a garment contacting major surface. Pressure sensitive adhesive element means are disposed longitudinally and centrally upon the garment contacting surface and extend from end to end thereof. The removable release strip overlies the entire length of the pressure sensitive adhesive element. At least one extreme end portion of the pressure sensitive adhesive element is provided with a pattern of raised and depressed areas whereby the resistance to peeling of both the release strip prior to use and the nether garment after use is lower in the end portion than in the central portion of the adhesive element.

7 Claims, 6 Drawing Figures

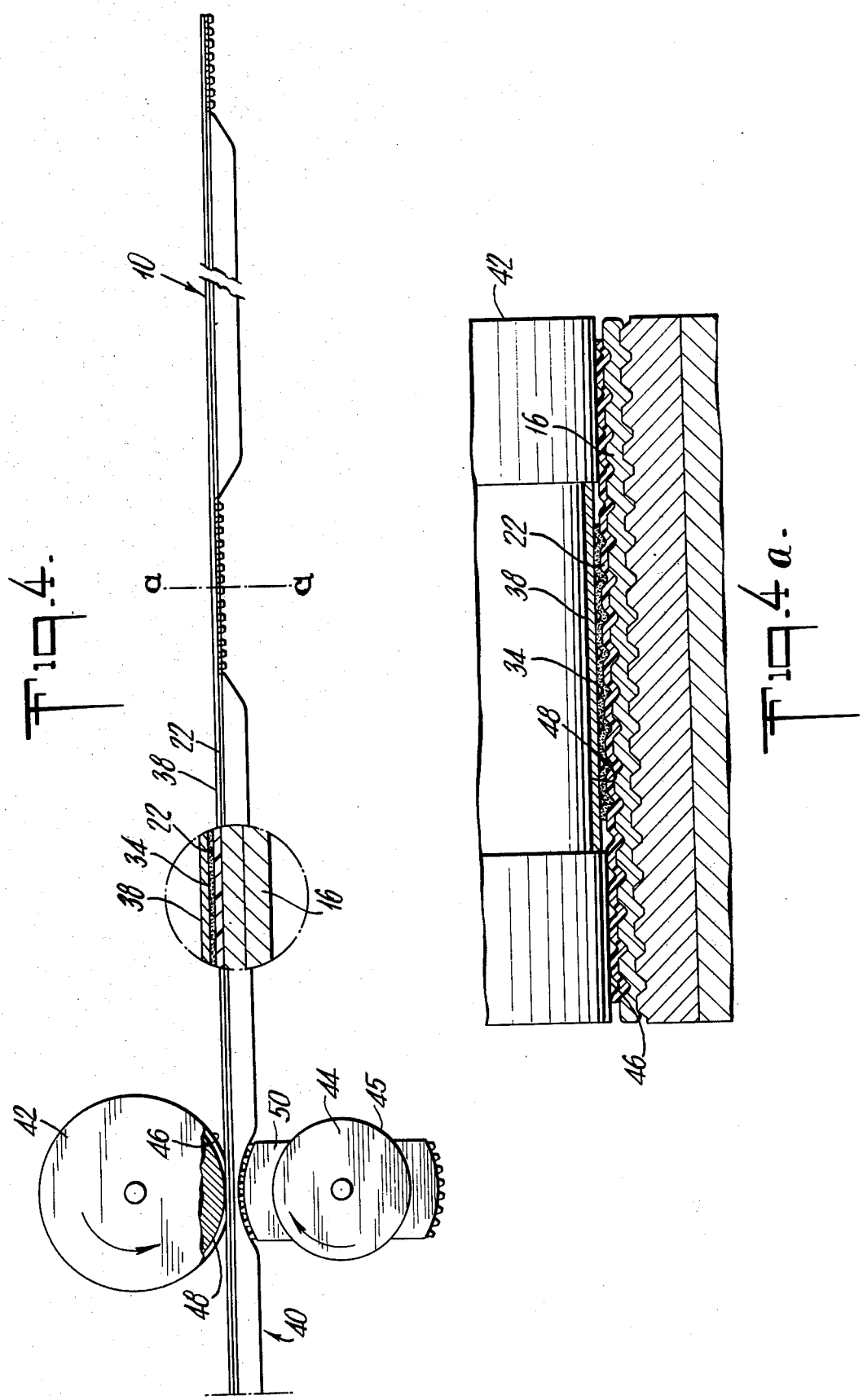

ADHESIVELY ATTACHED ABSORBENT LINERS

BACKGROUND OF THE INVENTION

This invention relates to absorbent nether garment liners such as sanitary napkins and panty shields and more specifically, to such products which employ adhesive means for attaching the product to the crotch portion of a nether garment when in use. Such products are provided to absorb and retain body fluids and to protect the nether garment from staining and soiling. The prior art is now replete with suggestions for absorbent liners comprising an absorbent body having garment and body contacting major surfaces and provided with pressure sensitive adhesive means on the garment contacting surface for adherence of the product to a nether garment. Generally, these liners are provided with a protective release strip overlying the pressure sensitive adhesive element and protecting it from dirt and unintentional adhesion when packaged, stored and handled prior to use. At the time of use, the strip is peeled from the adhesive means and the product is positioned and adhered to the undergarment. After use, the product is peeled from the undergarment and disposed of.

The adhesive system employed in such products must meet several sometimes conflicting criteria. In use, it is important that the product adhere tenaciously to the undergarment at all times and so the adhesive system must resist moisture, the sudden torques exerted by movements of the body and the frictional shearing forces exerted by the movements of the various layers of clothing worn by the user. Notwithstanding the adherence tenacity required of the adhesive system during use, it is important tha the protective strip be easily peeled from the adhesive prior to use without tearing or delaminating the product. After use, it is essential that the product be easily peeled from the undergarment, again without tearing or delaminating the product or, in this case, without doing damage to the fabric of the undergarment. In view of the fact that after use, the product is generally soiled, it is important that the user can easily and quickly grip the product and peel it from the garment without undue fumbling or effort.

Several solutions have been offered to this problem of providing in-use tenacity in combination with facile peelability. For example, in U.S. Pat. No. 3,897,783, issued to J. A. Ginocchio on Aug. 5, 1975, the adhesive element provided therein terminated in peaks which resulted in a decreased peeling force at the peaked terminal portions. This adhesive pattern was applied by employing a specifically designed adhesive applier. While this solution is generally effective, it suffers from the drawback of requiring intermittent application of adhesive, it is generally preferred in high speed operations to perform such a step continuously.

Still another solution to the problem is to provide a product with a so-called "dry edge". This method is exemplified in U.S. Pat. No. 3,672,371, issued on June 27, 1972 to R. J. Roeder and in U.S. Pat. No. 3,881,490, issued on May 6, 1975 to H. A. Whitehead and R. V. Braun. In both these instances, the adhesive element does not extend the full longitudinal length of the product, but instead ends some distance therefrom. On the other hand, the adhesive element is covered by a protective strip which extends beyond the ends of the adhesive element. Accordingly, prior to use the ends of the release strip are not adhered to the adhesive and are free to be gripped for removal. In use, the end portions of the product are not adhered to the garment but instead, are also free to be gripped for removal. While these unadhered ends do in fact allow for easier peeling of both the release strip prior to use and of the product from the undergarment during use, there are drawbacks. The release strip is generally stiffer than the remainder of the product and so the unadhered ends of the strip tend to stand away from the product and tend to "catch" on each other so that the product cannot be easily handled during production and packaging. This problem is particularly acute in the products such as the so-called three-dimensional curved garment liners as are described in a commonly assigned U.S. patent application having a serial number yet to be determined. The curvature of these napkins causes the stiffer release strip material to stand away even further. During use, the unadhered ends of the product provide a starting point for the undesirable detachment and displacement of the entire product under the forces exerted by body and garment movements.

It can thus be seen that, prior art efforts notwithstanding, a completely satisfactory solution to the apparently conflicting criteria in-use tenacity and easy peelability has heretofore been unavailable.

SUMMARY OF THE INVENTION

In accordance with the present invention, an adhesively attached protective absorbent liner for nether garments is provided uith means for allowing the product to be tenaciously held in place during use, but which can still be easily peeled to separate the product from both the release strip and the garment, all without the drawbacks encountered in prior art suggestions. The liner may comprise a generally elongated absorbent body having a body contacting major surface (i.e., the surface intended to be worn against the body) and a garment contacting major surface, i.e., the surface intended to be adhered to the crotch portion of a nether garment. Means are provided for securing the liner to the nether garment, these means comprising a pressure sensitive adhesive element disposed longitudinally on the garment contacting surface and extending substantially from end to end of that surface. A removable protective release strip is provided overlying the pressure sensitive element to protect the element from dirt and unintentional adhesion prior to use. In accordance with the teachings of this present invention, at least one extreme end portion of the pressure sensitive adhesive element is provided with a pattern of raised and depressed areas (i.e., raised and depressed with respect to each other) whereby the resistance to peeling of both the release strip and the nether garment is lower in this end portion than in the central portions of the adhesive element. Preferably both end portions are provided with such a pattern.

In perhaps its simplest embodiment, the adhesive element is disposed on the garment contacting surface and is provided in its end portions with the prescribed pattern of raised and depressed areas by embossing these portions using an embossing roller having such a pattern cut or etched into its surface. The release strip is then applied to the adhesive element overlying both the end portion and the unembossed central portion and will adhere to both portions so as to lie against the product during production and packaging without "catching" or otherwise getting in the way. Notwithstanding this, it has been found that the release strip clings far less tenaciously to the embossed areas than to the unembossed areas and hence, the ends provide easy starting points for removing the release stip. In fact, the strip may be removed for all practical purposes with the same facility as the so-called "dry edge" products but without any of the drawbacks. In use, the product may be placed and adhered to the crotch portion of an undergarment and, owing to the presence of adhesive extending to substantially the very ends, the product will be adhered along its entire length without leaving unadhered ends which could start the detachment of the entire product. Notwithstanding this total longitudinal adherenece, the embossed end portion will cling less tenaciously to the fabric of the garment than the central unembossed portions and hence, can be easily peeled therefrom thereby conveniently providing a starting edge for gripping and peeling the remainder of the product from the garment.

In a more specific embodiment, the embossing is extended across the entire end of the product to include those areas adjacent to the adhesive element. This extension of the embossing is, in fact, from production point of view, easier to accomplish than limiting the embossed areas to the adhesive and provides the additional advantage of giving the embossed ends of the product z directional strength, i.e., strength in the direction perpendicular to the plane of the major surfaces.

Also described in detail herein is a method for manufacturing the product of this invention without the need for fist embossing the adhesive area and then applying the release strip. Instead, the release strip is applied to the entire product assembly and the ends of the product are embossed in such a manner as to leave the release strip unembossed while still imprinting the embossing pattern on the adhesive.

BRIEF DESCRIPTION OF THE INVENTION

Referrring to the drawings:

FIG. 4 is a schematic longitudinal cross sectional view of a portion of a machine line for producing the garment liner of this invention;

FIG. 4A is a schematic, transverse cross sectional view of the machine line FIG. 4 taken through line a—a; and FIG. 4bis a perspective view of the top surface of the embossing roll shown in FIG. 4a.

DETAILED DESCRIPTION OF THE INVENTION

Figure 1:
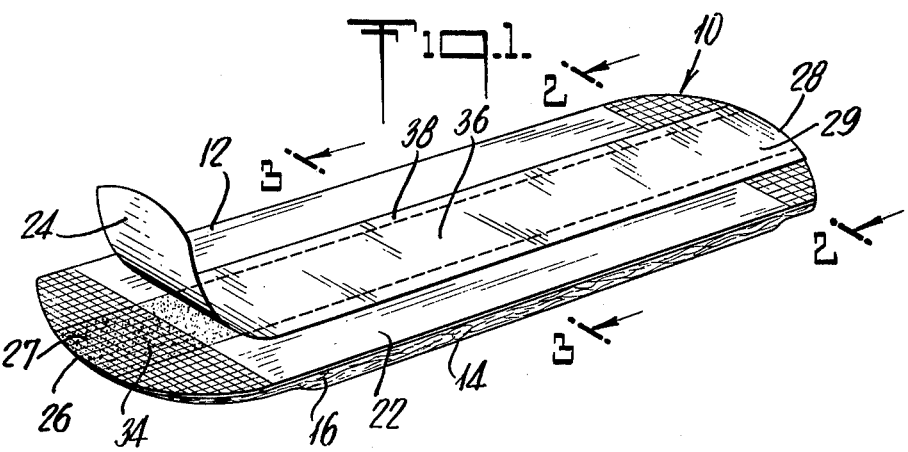
FIG. 1 is a perspective view looking down on the garment contacting surface of an absorbent nether garment liner embodying the teachings of this invention and showing the release strip partially peeled therefrom.
Figure 2:
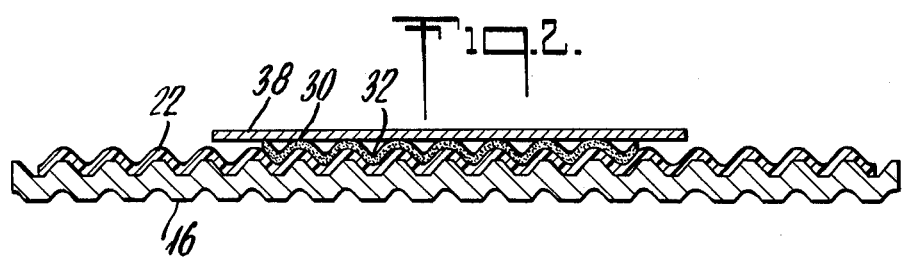
FIG. 2 is a sectional view of the garment liner of FIG. 1 taken along line 2—2.
Figure 3:
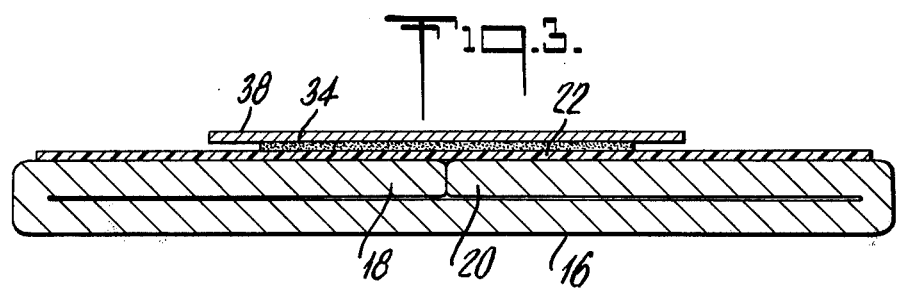
FIG. 3 is a sectional view of the garment liner of FIG. 1 taken along line 3—3.

FIGS. 1–3 illustrate an exemplary embodiment of the invention. Specifically depicted is an absorbent nether garment liner 10 with the garment contacting major surface 12 facing upwardly in the drawings and the body contacting major surface 14 facing downwardly. The liner 10 comprises an absorbent body 16 which may be made up of any suitable absorbent material such as, for example, comminuted wood pulp fibers, cotton linters, rayon fibers, cotton staple, blended sulfite creped wadding and the like. The absorbent body may even comprise synthetic absorbent materials such as the newly developed hydrophilic polyurethane foams. When employing absorbent matter in loosely associated particulate form such as comminuted wood pulp or crumbs of polyurethane foam, the particulate matter should be enclosed in a wrapper material which can be a fluid pervious woven material such as gauze, for example, or a nonwoven material, such as the ones described in U.S. Pat. No. 3,554,788 issued on Jan. 12, 1971 to M. R. Fechillas which has the added advantage of being flushable, i.e., may be disposed of by dispersing and flushing away in a water closet. Typical absorbent bodies comprising loosely associated absorbent particles enclosed in a fluid pervious wrapper are described in the aforementioned U.S. Pat. 3,897,783 issued to J. A. Ginocchio on Aug. 5, 1975.

In the absorbent body 16 illustrated in FIGS. 1–3, still another form of absorbent material is employed by way of example, this material being specifically the lofty and soft nonwoven through-bonded fabric described in U.S. Pat. No. 3,663,238 issued on May 16, 1972 to G. J. Liloia et al. This fabric consists essentially of a mixture of approximately 25% by weight of long (about 20.2 cms) rayon fibers and about 75% by weight of short (about 0.02 cms) wood pulp fibers and has a water dispersible binder applied throughout in an amount between about 1 percent and about 30 percent of the weight of the fibers on a dry solids basis. The binders of choice are of the self-curing acrylic latex family, the urethane family or other binders which can be utilized in low viscosity solutions or suspensions. The fabric has a weight of less than about 8 ounces per square yard and a density of about 0.15 about 0.05 gm. per cc. and may be characterized as being absorbent and extremely soft and lofty. Because of the through bonding, the fabric is capable of maintaining its structural integrity without the need of a wrapper material which, in the embodiment of FIGS. 1—3, has accordingly been dispensed with. As is best illustrated in FIG. 3, a double thickness of the fabric is employed by folding the longitudinal peripheral edges 18, 20 of a sheet of the fabric toward the center to form the absorbent body 16. These edges may be held in place by the application of adhesive or other means known in the art (not shown).

Overlying and in juxtaposition with the garment contacting surface of the absorbent body 16 is a fluid impervious layer 22 which is provided to act as a barrier to body fluids and prevent the "strike through" of such fluids onto the nether garment. This layer may comprise any thin flexible impermeable material such as, for example, a polymeric film, e.g., polyethylene, polypropylene, cellophane or even a normally fluid pervious material that has been treated to be impervious such as impregnated fluid repellent paper. It will be appreciated by one skilled in the art that in the case of the unwrapped, bonded fabric illustrated in FIGS. 1–3, the impervious layer 22 is best applied on the garment contacting side of the absorbent body 16 whereas, in the case of a wrapped product, the impervious layer may also be placed between the absorbent material and the wrapper or within the absorbent material. In some instances, the impervious layer may make up a portion of the wrapper itself as is the case in the product currently available from the Personal Products Company of Milltown, N.J. and sold by them as STAYFREE* Minipad sanitary napkins.

In any event, disposed upon the garment contacting major surface of the absorbent body 16 is a longitudinally, centrally located pressure sensitive adhesive element 24 which extends from one end 26 of the liner 10 to the other end 28 and is provided for attaching the liner to a nether garment. This adhesive element may comprise any of a large number of pressure sensitive adhesives already available on the market, including, for example, the water based pressure sensitive adhesives such as the acrylate adhesives, for example, vinyl acetate-2ethyl hexyl acrylate copolymer which is generally combined with tackifiers such as, for example, ethylene amine. Alternatively, the adhesive may comprise the rapid-setting thermoplastic (hot melt) adhesives such as block copolymers exemplified by styrene and butadiene styrene copolymers. The adhesive element may also comprise a two sided adhesive tape and the advantages of this invention will accrue equally well to this configuration.

In accordance with the teachings of this invention and as best illustrated in FIG. 2, the end portions 27 and 29 of the adhesive element 24 are provided with a pattern of raised areas 30 and depressed areas 32. This pattern is best imposed upon the end portions of the adhesive element by passing the ends of the liner between an embossing roll and an anvil roll, as will be described in greater detail below. In any event, in addition to imposing this pattern upon the adhesive, the embossing process likewise imposes such a pattern upon the areas of the liner 34 adjacent to the end portion of the adhesive. This is particularly advantageous in that such embossing gives these end portions a substantial increase in resistance to delamination, a property highly desirable for the ends of the liner which ends are generally gripped when applying and removing the product. As best illustrated in FIG. 3, the central portion of the liner and consequently, the central portion 36 of the adhesive element 24 are free of this embossed pattern of raised and depressed areas and are essentially smooth and flat. The pattern may comprise, for example, about 1-30% of the total embossed area being raised and the remainder comprising the depressed area. Preferably, the raised area comprises about 5-20% of the total embossed area.

Overlying the full length of the adhesive element 24 is a protective release strip 38 which is provided to protect the adhesive element from dirt and from unintended adhesion prior to use. The strip may be of any suitable sheet-like material which adheres with sufficient tenacity to the adhesive element to remain in place, but which can readily be removed when the liner is to be used. A particularly useful material is a semibleached kraft paper, the adhesive contacting side of which has been silicone coated to provide for easy release from the adhesive element 24. As is shown in FIG. 3, the release strip 38 makes close contact with the entire surface of the unembossed central portion of the adhesive element 24. In contrast thereto, referring to FIG. 2, the release strip 38 tends to rest on only the raised areas 30 of the embossed end portions of the adhesive. It has been discovered that the release strip 38 will adhere to all portions of the adhesive element 24 with sufficient tenacity to allow for facile handling of the product during production and prior to use. The tenacity of this adherence, however, has been found to vary to a significant degree between the embossed end portions and the unembossed central portions, the latter portions being significantly more tenacious than the former. Because of this lesser degree of adherence at the ends of the liner, the release strip can be peeled away easily from the embossed portions of the adhesive element 24. Once the peeling of the release strip has been initiated, the partially peeled strip can now be firmly gripped and completely peeled from the more tenacious central portion of the adhesive element 24.

As has been described above, one method of obtaining the prescribed pattern of raised and depressed areas in the end portions of the adhesive is to pass the ends of the product through the nip of embossing rollers. This can be done prior to applying the release strip to the product and the described effect of having the release strip rest predominantly upon the raised portions of the embossed adhesive will be obtained. It is desirable, however, for the purposes of high speed production, to form a long completed laminate of all of the layers of the product, i.e., the absorbent body, the adhesive element and the release strip, and then to cut individual products from this laminate. Accordingly, a method has also been provided for performing the prescribed embossing upon the completed laminate (including the release) strip) without concomitantly forcing the release strip into the depressed areas of the embossed adhesive.

Referring now to FIG. 4, illustrated there is a schematic view of a machine line employing such a method. A laminate 40 is moved from left to right in the drawing in the direction of the arrow. The laminate comprises the absorbent body 16 having the fluid impervious layer 22 thereon. The pressure sensitive adhesive element 24 is applied to the layer 22 and the release strip 38 overlies this adhesive element. The laminate 40 is passed through the nip of two rotating rollers; an anvil roller 42 is and an embossing roller 44. The anvil roller 42 is provided with a substantially smooth surface 46 around its entire circumference with the exception of an undercut portion 48, as best seen in FIG. 4a. The undercut portion 48 is of essentially the same width and depth as the width and thickness of the release strip and is adapted to accommodate the release strip 38 therein as the laminate passes into the nip of the two rollers.

Figure 4B:
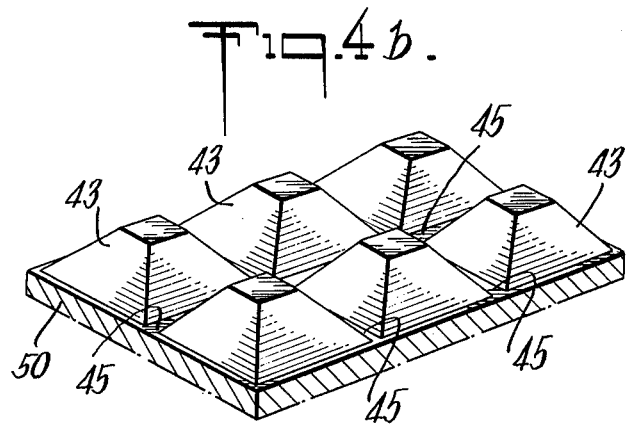

The embossing roller 44 is provided with an embossing section 50 which projects from the periphery of a portion of the circumference of the roller 44 and is provided on its circumferential surface with the desired pattern of raised and depressed area to be imposed upon the laminate. Referring to FIG. 4b shown there in perspective view is the top surface of the embossing section. The pattern of raised areas in this case take the form of truncated pyramids 43 whereas the depressed areas are the spaces 45 between pyramids. It will be apparent to one skilled in the art that this is only one of many possible patterns by which the benefits of this invention may be obtained.

In operation, as the laminate is passed between the rollers, the embossing rollers will impress the desired pattern upon the laminate in space intervals determined by the portion of the circumference of the roller 44 which is occupied by the embossing section 50.

The rollers are spaced apart so that the distance between the flat surface 46 of the anvil 42 and the surface 45 of the embossing roller 44 which is not provided with the embossing section 50 is approximately 0.1 to 0.2 inches thick and the release strip approximately 0.001 to 0.008 inches thick. The rollers will be spaced apart as described above a distance of about 0.01 to 0.02 inches or more. Normally, a nip pressure between the two rollers is in the order of about 5,000 to 200,000 pounds per square inch and may be developed for example, by spring loading one roller against the other.

In operation, as the laminate is passed between the rollers, the desired pattern will be impressed in spaced intervals, the spacing of which is determined by the portion of the circumference of the embossing roller 44 occupied by the embossing section 50. Because the release strip 38 is accommodated within the undercut 48 of roller 42, the strip is essentially uneffected by the embossing operation. It has been discovered that even though only the embossing roller is provided with the pattern of raised and depressed areas and the anvil roller is provided with an essentially flat surface, the pattern imposed upon the embossed portion of the laminate is that illustrated in FIG. 2. That is to say, both the top and bottom surfaces of the embossed portion of the laminate after it leaves the nip of the embossing rolls exhibit raised and depressed areas. The release strip, uneffected by the embossing process, rests upon the raised areas, as is illustrated in FIG. 2.

The laminate 40, leaving the nip of the embossing rollers and having the embossing pattern imposed at intervals is next cut into individual liners by cutting means (not shown) which pass transversely through the embossed portions of the laminate. Such cutting means, which form no part of the inventive features of this invention may comprise any such means well known to those skilled in the art, as for example, rotary knives or die cutters.

The advantages of this invention are further illustrated by the following example.

EXAMPLE

A laminate is prepared in the form shown in FIG. 4 and is embossed with the pattern illustrated in connection with this figure. The absorbent body comprises the nonwoven fabric described in the aforementioned U.S. Pat. No. 3,663,230. The fluid impervious layer is a film of polyethylene having a thickness of 2 mils and the adhesive is of the hot melt type. Approximately 10 percent of the embossed adhesive area constitutes raised areas. The release strip is the silicone coated paper described above. The laminate is approximately two inches wide and 0.125 inches thick in the unembossed areas. The embossed areas are approximately 0.035 inches thick. The adhesive element is approximately 0.75 inches wide and the release paper overlying the adhesive element is about 1.0 inches wide.

A series of five samples are cut from this partially embossed laminate. Each of the samples comprise an unembossed length of 2.5 inches followed by an embossed length of 1.75 inches which in turn is followed by an unembossed length of 2.5 inches. Each of these samples is to be tested to determine the force required to continuously peel the release strip from the remainder of the sample. The test procedure used is to adhere each sample, garment contacting side up, to a stainless steel plate by means of double faced adhesive tape. A clip is then attached to the leading end of the release strip, which clip is then in turn attached, by means of a string, to the jaws of an Instron Tester. The string is so arranged as to provide a peeling angle of 180°. The jaws of the Instron Tester are operated at a peeling rate of two inches per minute and the Instron is equipped with a recorder-plotter which plots the force-distance function of each peel test. The peeling is carried out for all five samples and then the average force recorded over all the unembossed adhesive areas for all of the samples is determined by arithmetic averaging of the values read from the plot.

The arithmetic average for all the embossed areas of the adhesive is determined in the same manner. The test results are that the average force for the embossed areas is 18.1 gms. as contrasted with an average value of 84.9 gms. for the unembossed area. Thus, it can be seen that the release strip clings far less tenaciously to the embossed areas as compared to the unembossed areas. This notwithstanding, the release strip clings to the embossed area to a sufficiently tenacious degree to remain adhered thereto during production and subsequent handling.

We claim:

1. A protective absorbent liner for nether garments comprising:
    an elongated absorbent body having a body contacting major surface and a garment contacting major surface;
    means for securing said liner to the interior of the crotch portion of said nether garment, said means comprising a pressure sensitive adhesive element disposed upon said garment contacting surface and extending longitudinally and substantially, from end to end on said garment contacting surface;
    a removable protective release strip overlying said pressure sensitive adhesive element;
    at least one end portion of said pressure sensitive adhesive elements being provided with a pattern of raised and depressed areas whereby the resistance to peeling of both the the release strip and the nether garment is lower in said end portion than in the central portion of said adhesive element.

2. The protective liner of claim 1 wherein the portion of said release strip overlying the at least one extreme end portion of said pressure sensitive adhesive element rest on said raised area.

3. The protective liner of claim 1 wherein both extreme end portions of said pressure sensitive adhesive element are provided with said pattern of raised and depressed areas.

4. The protective liner claim 1 wherein said raised areas comprise about 1.0 to about 30% of the total adhesive area provided with said pattern.

5. The protective liner of claim 4 wherein said raised areas comprise about 5.0 to about 20% of the total adhesive area provided with said pattern.

6. The protective absorbent liner of claim 1 wherein said absorbent body comprises an absorbent material having a fluid impervious layer overlying and adhered to the garment contacting major surface.

7. The protective absorbent liner of claim 6 wherein said fluid impervious layer is polyethylene film.

* * * * *

UNITED STATES PATENT AND TRADEMARK OFFICE
CERTIFICATE OF CORRECTION

PATENT NO. : 4,023,570
DATED : May 17, 1977
INVENTOR(S) : Kays Chinai et al

It is certified that error appears in the above-identified patent and that said Letters Patent are hereby corrected as shown below:

In Column 1, line 35, "tha" should read --- that ---.

In Column 2, line 30, "uith" should read --- with ---.

In Column 3, line 3, "stip" should read --- strip ---.

In Column 3, line 13, "portion" should read --- portions ---.

In Column 3, line 22, "from production" should read --- from a production ---.

In Column 3, line 31, "fist" should read --- first ---.

In Column 3, line 53, "machine line Fig.4" should read --- machine line of Fig.4 ---.

In Column 4, line 11, "being flushable" should read --- being water flushable ---.

In Column 4, line 21, "U.S.Pat.No.3,663,238" should read --- U.S.Pat.No.3,663,348 ---.

In Column 4, line 34, "about 0.15 about 0.05" should read --- about 0.15 to about 0.05 ---.

In Column 6, line 23, "release) strip)" should read --- release strip) ---.

In Column 6, line 23, "concomittantly" should read --- concomitantly ---.

In Column 6, line 35, after "42" the word "is" should be deleted.

UNITED STATES PATENT AND TRADEMARK OFFICE
CERTIFICATE OF CORRECTION

PATENT NO. : 4,023,570
DATED : May 17, 1977
INVENTOR(S) : Kays Chinai et al

It is certified that error appears in the above-identified patent and that said Letters Patent are hereby corrected as shown below:

In Column 6, line 62, "anvil 42" should read --- anvil roller 42 ---

In Column 6, line 64, the following lines have been omitted, --- equal to the thickness of the laminate exclusive of the release strip. For example, the entire laminate may be approximately ---.

In Column 6, line 68, "0.01 to 0.02" should read --- 0.1 to 0.2 ---.

Signed and Sealed this

Twenty-ninth Day of August 1978

[SEAL]

Attest:

RUTH C. MASON
Attesting Officer

DONALD W. BANNER
Commissioner of Patents and Trademarks